US012672770B2

(12) United States Patent
Marmon et al.

(10) Patent No.: US 12,672,770 B2
(45) Date of Patent: Jul. 7, 2026

(54) LARYNGOSCOPE AND USES THEREOF

(71) Applicant: Children's National Medical Center, Washington, DC (US)

(72) Inventors: Louis Marmon, Potomac, MD (US); Marjorie Brennan, McLean, VA (US); Niya Khanjar, Elkton, MD (US); Catherine Schilling, East Northport, NY (US); Dhatri Saamak, Woodstock, MD (US); Joseph Lipari, Frederick, MD (US); Zain Shamsuddin, Ijamsville, MD (US)

(73) Assignee: Children's National Medical Center, Washington, DC (US)

( * ) Notice: Subject to any disclaimer, the term of this patent is extended or adjusted under 35 U.S.C. 154(b) by 50 days.

(21) Appl. No.: 18/656,003

(22) Filed: May 6, 2024

(65) Prior Publication Data

US 2024/0366081 A1 Nov. 7, 2024

Related U.S. Application Data

(60) Provisional application No. 63/500,368, filed on May 5, 2023.

(51) Int. Cl.
| | |
|---|---|
| *A61B 1/267* | (2006.01) |
| *A61B 1/00* | (2006.01) |
| *A61B 1/07* | (2006.01) |

(52) U.S. Cl.
CPC .......... *A61B 1/267* (2013.01); *A61B 1/00126* (2013.01); *A61B 1/00128* (2013.01); *A61B 1/07* (2013.01)

(58) Field of Classification Search
CPC ..... A61B 1/267; A61B 1/2673; A61B 1/2676; F16B 21/06; F16B 21/08
See application file for complete search history.

(56) References Cited

U.S. PATENT DOCUMENTS

| | | | | |
|---|---|---|---|---|
| 6,013,026 A | * | 1/2000 | Krauter | .................... A61B 1/07 |
| | | | | 600/199 |
| 6,350,235 B1 | * | 2/2002 | Cohen | .................. A61B 1/0669 |
| | | | | 600/199 |

(Continued)

FOREIGN PATENT DOCUMENTS

| | | | | | |
|---|---|---|---|---|---|
| EP | 2497407 A1 | * | 9/2012 | ............. | A61B 1/267 |
| GB | 2491189 A | * | 11/2012 | ........... | A61B 1/0669 |

*Primary Examiner* — Eduardo C Robert
*Assistant Examiner* — Anna V. Little
(74) *Attorney, Agent, or Firm* — Oblon, McClelland, Maier & Neustadt, L.L.P.

(57) ABSTRACT

A laryngoscope, including a blade having a flat top surface and a bottom surface extending from a base of the blade and a first vertical projection and a second vertical projection at the base of the blade extending from the bottom surface of the blade and a connector configured to couple to a handle of the laryngoscope and further configured to couple to the base of the blade via a first opening configured to receive the first vertical projection and a second opening configured to receive the second vertical projection, wherein the base of the blade and a first portion of the blade are transparent or translucent and a second portion of the blade is opaque, and the base of the blade further includes a cutout aligned with a channel in the connector between the first opening and the second opening when the blade is coupled to the connector.

20 Claims, 4 Drawing Sheets

(56)        References Cited

U.S. PATENT DOCUMENTS

| 2005/0240081 A1* | 10/2005 | Eliachar ................. A61B 1/267 |
| | | 600/199 |
| 2005/0279355 A1* | 12/2005 | Loubser ................. A61B 1/051 |
| | | 128/207.14 |
| 2008/0234549 A1* | 9/2008 | Geist ...................... A61B 1/267 |
| | | 600/194 |
| 2018/0168433 A1* | 6/2018 | Meyer ................ A61B 1/00016 |
| 2019/0133430 A1* | 5/2019 | Inglis ................... A61B 1/0005 |
| 2019/0175008 A1* | 6/2019 | Nagele .............. A61B 1/00183 |
| 2020/0246102 A1* | 8/2020 | Weinmann ............. A61B 1/018 |

* cited by examiner

200

200

200

LARYNGOSCOPE AND USES THEREOF

CROSS-REFERENCE TO RELATED APPLICATIONS

The present application claims priority to U.S. Provisional Application No. 63/500,368, filed May 5, 2023, which is incorporated herein by reference in its entirety for all purposes.

BACKGROUND

Field of the Disclosure

The present disclosure relates to laryngoscopes.

Description of the Related Art

Laryngoscopy typically involves examination of the larynx and vocal cords and can be used to facilitate intubation with an endotracheal tube. Laryngoscope blades can be used to provide a clear visualization of the larynx by removing obstructive anatomy and providing artificial illumination.

The foregoing "Background" description is for the purpose of generally presenting the context of the disclosure. Work of the inventors, to the extent it is described in the background section, as well as aspects of the description which may not otherwise qualify as prior art at the time of filing, are neither expressly nor impliedly admitted as prior art against the present disclosure.

SUMMARY

The foregoing paragraphs have been provided by way of general introduction and are not intended to limit the scope of the following claims. The described embodiments, together with further advantages, will be best understood by reference to the following detailed description taken in conjunction with the accompanying drawings.

In one embodiment, the present disclosure is related to a laryngoscope, comprising: a blade having a flat top surface and a bottom surface extending from a base of the blade and a first vertical projection and a second vertical projection at the base of the blade extending from the bottom surface of the blade; and a connector configured to couple to a handle of the laryngoscope and further configured to couple to the base of the blade via a first opening, the first opening being configured to receive the first vertical projection and a second opening configured to receive the second vertical projection, wherein the base of the blade and a first portion of the blade are transparent or translucent and a second portion of the blade is opaque, and the base of the blade further includes a cutout aligned with a channel in the connector between the first opening and the second opening when the blade is coupled to the connector.

In one embodiment, the present disclosure is related to a laryngoscope, comprising a curved blade having a flat top surface and a bottom surface extending from a base of the curved blade and a first vertical projection and a second vertical projection at the base of the curved blade extending from the bottom surface of the curved blade; and a connector configured to couple to a handle of the laryngoscope and further configured to couple to the base of the curved blade via a first opening, the first opening being configured to receive the first vertical projection and a second opening configured to receive the second vertical projection, wherein the base of the curved blade and a first portion of the curved blade are transparent or translucent and a second portion of the blade is opaque.

In one embodiment, the present disclosure is related to a laryngoscope, comprising: a blade having a flat top surface and a bottom surface extending from a base of the blade and a first vertical projection and a second vertical projection at the base of the blade extending from the bottom surface of the blade; and a connector configured to couple to a handle of the laryngoscope and further configured to couple to the base of the blade via a first opening, the first opening being configured to receive the first vertical projection and a second opening configured to receive the second vertical projection, wherein the base of the blade and a first portion of the blade are transparent or translucent and a second portion of the blade is opaque.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
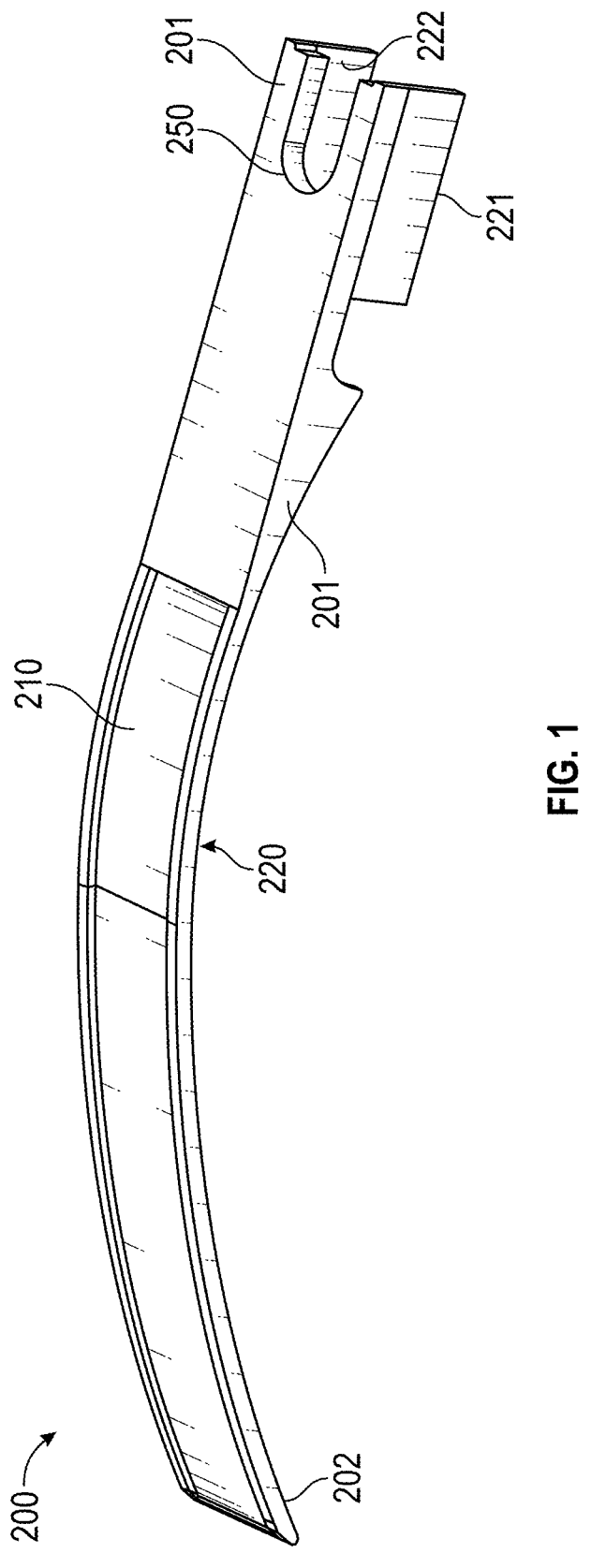
FIG. 1 is an illustration of a laryngoscope blade, according to one embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Laryngoscopes can be used to visualize and treat pathology in the vocal cords and/or the throat. Laryngoscopy is a common diagnosis modality for a number of conditions, including trouble swallowing or breathing, voice changes, coughing, persistent throat pain, and bad breath. These conditions are common with pediatric patients. Laryngoscopy can also be used to investigate the throat in conjunction with internal imaging.

A laryngoscope can include a blade that is coupled to a handle at approximately a right angle to the handle. The blade can be inserted into a patient's mouth during a laryngoscopy when the patient is lying down (supine) with their head tilted at an angle. A user of the laryngoscope can hold the laryngoscope by the handle and insert the blade into the patient's mouth from above. The blade can then be maneuvered in the throat. A laryngoscope blade can be inserted while pressure is maintained on the device until the tip of the blade rests on the vallecula. Upward pressure can then be applied to the blade to lift the epiglottis and expose the larynx for visualization and physical access.

In one embodiment, the present disclosure is directed to a laryngoscope that is configured to provide an unobstructed view or path to the larynx. The laryngoscope can be configured to displace or restrict anatomical structures in the oral cavity or the throat. The restriction of the anatomical structures can result in an unobstructed view or path from the mouth to the larynx and associated structures such as the vocal folds and/or the glottis. The anatomical structures that are displaced or restricted can include, for example, the lips, the tongue, and the epiglottis, which covers the glottis. In one embodiment, the laryngoscope blade can displace an anatomical structure by pushing the structure towards the walls of the throat without damaging the structure or the throat. The path created by the laryngoscope blade can be used to visualize, image, or treat the larynx and surrounding features. For example, an instrument can be inserted into the mouth and advanced along the laryngoscope to the throat. In one embodiment, the laryngoscope can include a surgical device or tool, such as a laser or camera.

FIG. 1 is an illustration of a laryngoscope blade 200, according to one embodiment of the present disclosure. The blade 200 can have a base 201 and a tip 202 connected by the body of the blade. The base 201 of the blade can be coupled to the handle, and the tip 202 and body of the blade can be inserted into the mouth. In one embodiment, the tip can be pointed. In one embodiment, the tip can be rounded. In one embodiment, the tip 202 of the blade can be thicker than the body of the blade to form a tongue or spatula for insertion. In one embodiment, the blade 200 can have a first (upper, top) surface 210 and an opposing second (lower, bottom) surface 220. The designation of upper and lower surfaces can be understood to be non-limiting terms referring to a particular perspective or position of the blade. For example, the first surface can be an "upper" surface in that the first surface is nearer to the roof of the mouth of a patient when the blade is inserted. The first surface 210 and the second surface 220 can be joined by a first sidewall 201 and a second sidewall (not illustrated) opposite to the first sidewall 201. In one embodiment, the first surface 210 of the blade can be a flat surface without raised structures. In one embodiment, the blade 200 can be curved. The curvature of the blade 200 can begin and end at any point along the length of the blade. In one embodiment, the blade 200 can be straight with a curved tip. In one embodiment, the blade 200 can be symmetrical around a central axis that runs along the length of the blade 200. In one embodiment, the shape of the blade can be similar to a Miller blade, a Macintosh blade, or a Bizzari-Giuffrida blade.

In one embodiment, when the blade is inserted into the throat, an instrument can be advanced along the body of the blade. The instrument can be, for example, a camera or a surgical device. In one embodiment, the instrument can be advanced along the upper or lower surface of the blade. In one embodiment, the surfaces and sidewalls can form an inner channel or chamber such that the blade is partially or fully hollow.

In one embodiment, the base of the blade can include a first projection (panel, wall) 221 and a second projection (panel, wall) 222 extending downward in the same direction from the bottom surface of the blade. The first and second projections can be used to couple the blade to a connector. In one embodiment, the first and second side projections can strengthen the base of the blade compared to a blade that only has a single projection. The base can further include a cutout 250. The cutout 250 can be a rounded shape, as illustrated in FIG. 1. In one embodiment, the cutout 250 can form an opening for light to travel through the body of the blade.

In one embodiment, the laryngoscope can include an illumination source. The illumination source, such as a fiber optic cable, can be contained in the handle of the laryngoscope. In one embodiment, the handle can further include a battery for the illumination source. The fiber optic cable can provide illumination at the end of the handle where the base of the blade is coupled to the handle. In one embodiment, when the blade is coupled to the handle, the illumination source (e.g., fiber optic cable) can extend to the cutout 250 or past the cutout 250 to the first surface of the blade. The base and body of the blade can propagate light from the handle to the body or tip of the blade.

In one embodiment, the blade can be a transparent or translucent material. In one embodiment, at least one surface of the blade can be transparent or translucent. For example, the first surface 210 can be a transparent or translucent material. Light from the illumination source at the base of the blade can then propagate through the base of the blade and the transparent or translucent portion of the first surface 210. In one embodiment, the first surface 210 and the second surface 220 of the blade can be transparent or translucent. In this manner, the blade 200 can provide illumination through the body of the blade while maintaining a low or thin profile. The low profile of the blade can have functional advantages for laryngoscopy and can also reduce patient discomfort during and after a procedure.

In one embodiment, the transparent or translucent material can be a plastic, such as acrylic. The dimensions of the transparent or translucent portion of the blade can be configured so that the blade adequately illuminates a surrounding area without creating glare or overexposure that interferes with imaging and visibility of the surrounding area. In one embodiment, a light output along the blade and/or at the tip of the blade can be approximately 500 lux (lumens per square meter), per light standards for respiratory devices. In one embodiment, the light output can be between approximately 700 lux to approximately 900 lux for laryngoscope procedures.

In one embodiment, the blade can be coated with an opaque material to adjust the transparency of the blade. In one embodiment, the opaque material can be a metal. For example, the opaque material can be aluminum. Aluminum is highly biocompatible, opaque, lightweight, and cheap, and can be used for invasive medical devices. Using a uniform transparent or translucent material (e.g., acrylic) for the surfaces of the blade and adjusting the transparency of the blade via a coating of an opaque material (e.g., aluminum) can result in cheaper and more efficient manufacturing of the blade as a whole.

In one embodiment, the opaque material can coat a portion of the blade. The opaque portion can include, for example, a portion of the first surface 210 or the second surface 220. In one embodiment, the opaque portion can include the base of the blade. In one embodiment, the base of the blade can be left uncoated, e.g., fully transparent or translucent according to the material of the blade. In one embodiment, the transparent or translucent region can be a first portion of the circumference of blade (e.g., the top side of the blade), and the opaque region can be a remaining portion of the circumference of the blade (e.g., the bottom side of the blade).

In one embodiment, approximately one-third to approximately two-thirds of a length of the blade can be coated with the opaque material (e.g., aluminum) to provide a desired amount of illumination (e.g., 700 to 900 lux). The opaque region can extend from the tip of the blade towards the base of the blade. In one embodiment, the opaque region can be discontinuous. For example, a first opaque region at the tip of the blade and a second opaque region along the body of the blade can be coated in aluminum, while a region between the first and second opaque regions can be transparent or translucent. In one embodiment, less than one-third or more than two-thirds of the blade can be coated for opacity.

The flat and partially transparent blade as described herein can provide an advantage over laryngoscope blades that transmit and project light through a raised flange or shelf. Protruding structures along the top surface of a blade can obstruct the visibility and access to the throat when the blade is inserted. The structures can also result in difficulty advancing the blade into the throat. In addition, many blades having a flange for illumination can be asymmetrical, resulting in a handedness of the blade. In other words, a blade having an asymmetrical structure may be easier to use with one hand (e.g., right hand) and more difficult to use with the opposing hand (e.g., left hand). The handedness of the blade can result in the laryngoscope being less effective or useable as a universal tool. A symmetrical blade, as presented herein, can be used in the same manner with either hand while still providing necessary illumination and a clear visual path along the blade.

Figure 2A:
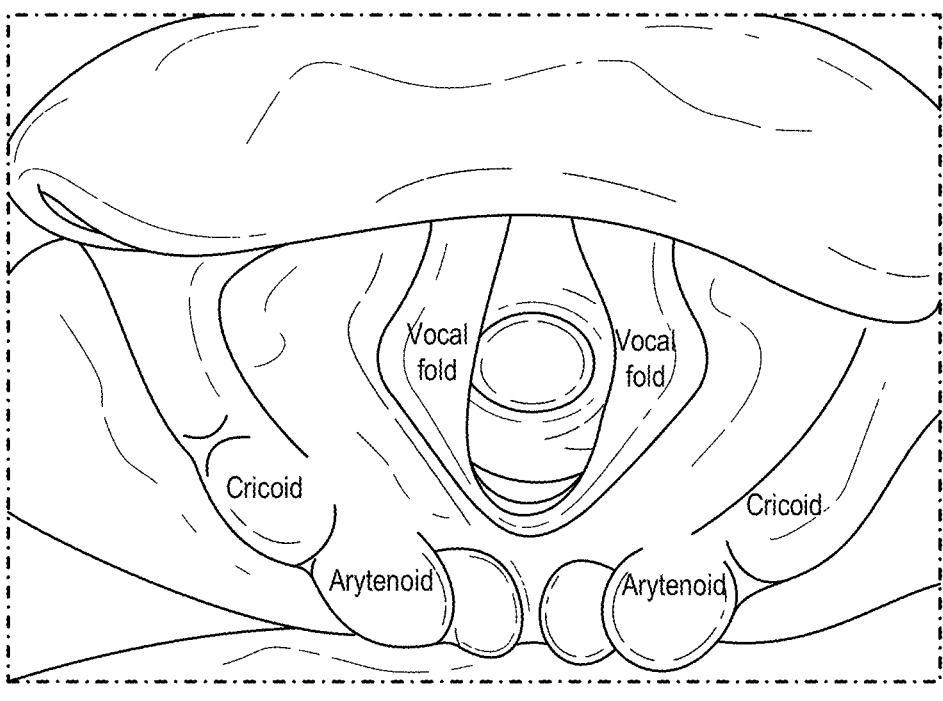
FIG. 2A is an image captured using a laryngoscope, according to one embodiment of the present disclosure.
Figure 2B:
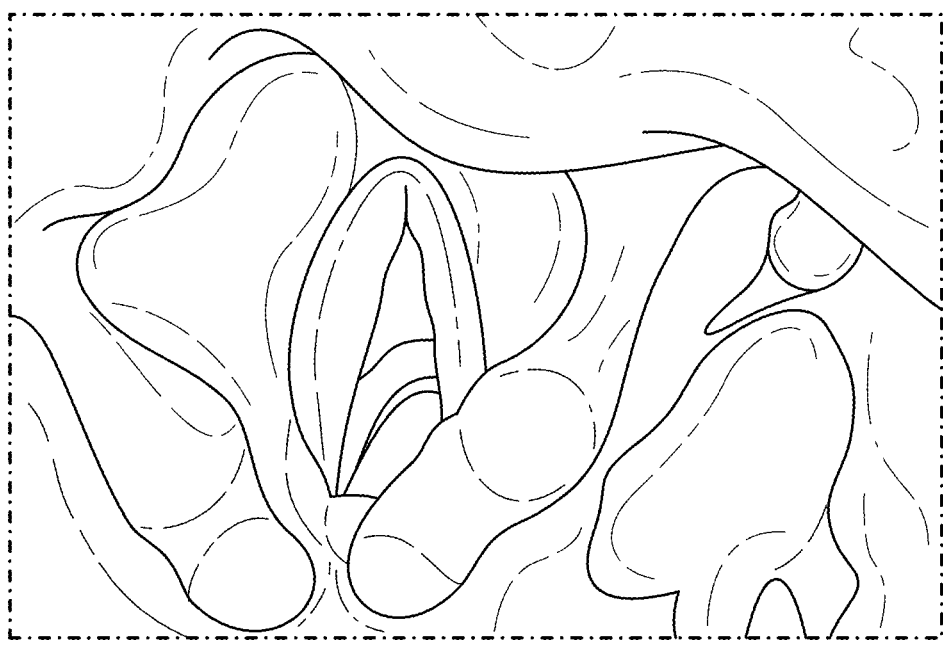
FIG. 2B is an obstructed image captured using a laryngoscope, according to one embodiment of the present disclosure.

In one embodiment, the laryngoscope blade of the present disclosure can provide an unobstructed view of the oral cavity, including structures such as left and right cricoid cartilage, left and right arytenoid cartilage, and left and right vocal folds surrounding the larynx. FIG. 2A is an image or visualization of the larynx obtained using the laryngoscope of the present disclosure according to one embodiment. The view can be illuminated via the transparent or translucent base and body of the blade. The view can be approximately symmetrical such that the left and right sides of the larynx are similarly visible and unobstructed. In contrast, FIG. 2B is an image of the larynx obtained using a traditional laryngoscope having a flange for illumination. The left side of the larynx is obscured by the flange and cannot be seen or accessed. The obstruction of the view can make it difficult for a user to make a clinical observation of the patient's upper airway and vocal cords. The obstruction by the flange can also impede the use of instruments or tools in conjunction with the laryngoscope.

Figure 3A:
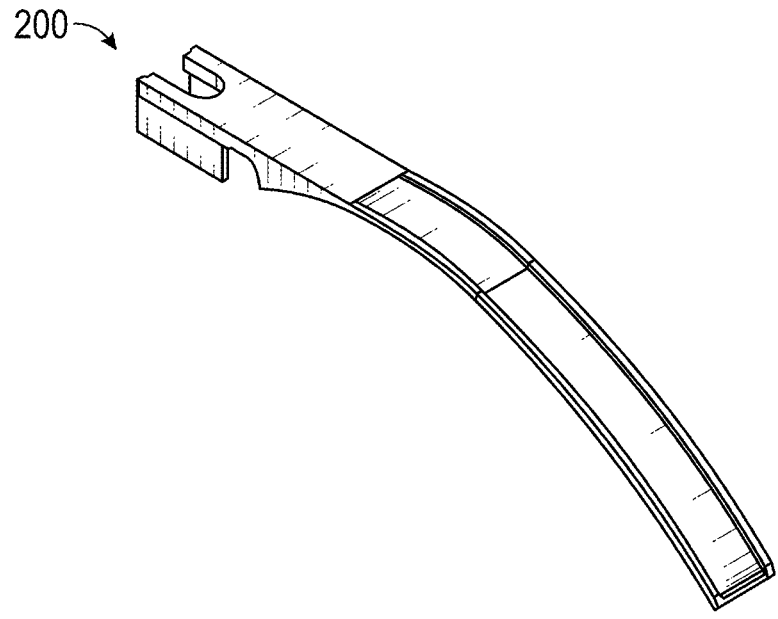
FIG. 3A is an illustration of a laryngoscope blade, according to one embodiment of the present disclosure.
Figure 3B:
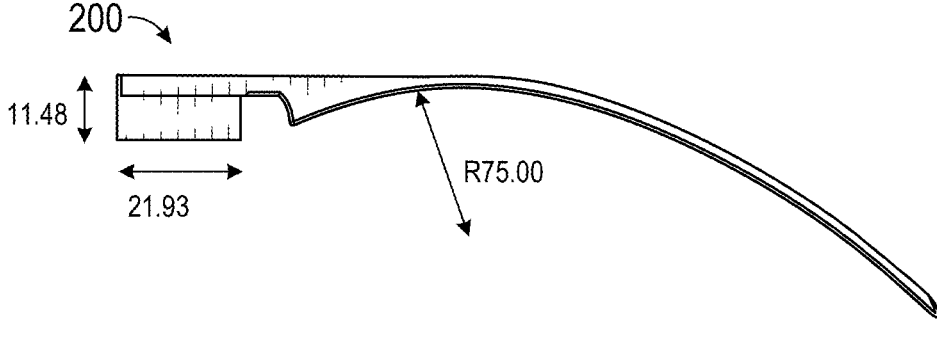
FIG. 3B is an illustration of a laryngoscope blade, according to one embodiment of the present disclosure.
Figure 3C:
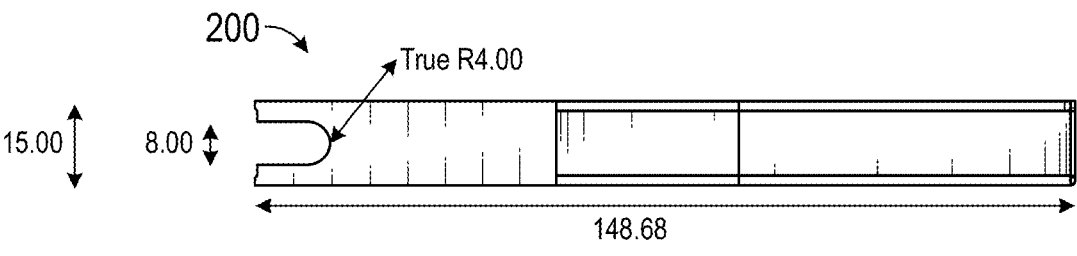
FIG. 3C is an illustration of a laryngoscope blade, according to one embodiment of the present disclosure.

FIG. 3A through FIG. 3C are illustrations of the blade 200, according to one embodiment. FIG. 3A is a top view of the blade 200. In one embodiment, the blade can be a first material (e.g., acrylic) and can be reinforced with a second material to increase the strength of the blade. In one embodiment, the second material can be a metal. For example, the second material can be aluminum. In one embodiment, the reinforcement can be a layer of the second material (e.g., aluminum) forming the bottom surface of the blade. In one embodiment, the reinforcement can include one or more structures attached to the base or bottom surface of the blade. In one embodiment, the blade can be reinforced to withstand a tensile force of approximately 150N. The reinforcement of the blade with the second material can allow the blade to be inserted into the larynx and displace the tongue and epiglottis without bending or breaking.

FIG. 3B is a side view of the blade 200. In one embodiment, the blade can be curved through the length for easier passage over the tongue and to expose the larynx without coming into direct contact with the epiglottis. In one embodiment, the curvature of the blade can follow a radius of approximately 75 millimeters (mm). In one embodiment, the curvature of the blade can vary throughout the length of the blade. In one embodiment, the projections can extend approximately 21.93 mm toward the body of the blade. In one embodiment, the base of the blade including the projections can have a height of approximately 11.48 mm. In one embodiment, the blade can be straight with a curved tip configured to pull the epiglottis aside (e.g., upward toward the roof of the mouth) in order to expose the larynx.

FIG. 3C is a top view of the blade 200. In on embodiment, the blade can be approximately 148.68 mm in length and approximately 15.00 mm wide. In one embodiment, the cutout 250 at the base of the blade can be approximately 8.00 mm wide with a radius of approximately 4.00 mm. In one embodiment, the dimensions of the blade can be such that the blade can be in contact with and restrict anatomical structures (e.g., the tongue, epiglottis) when inserted into the mouth. For example, the curvature of the blade can enable the blade to fit in the angled passageway between the base of the tongue and the back surface of the epiglottis. In one embodiment, the dimensions of the blade can be scaled for adult patients and for pediatric patients of varying ages and developmental stages.

Figure 4:
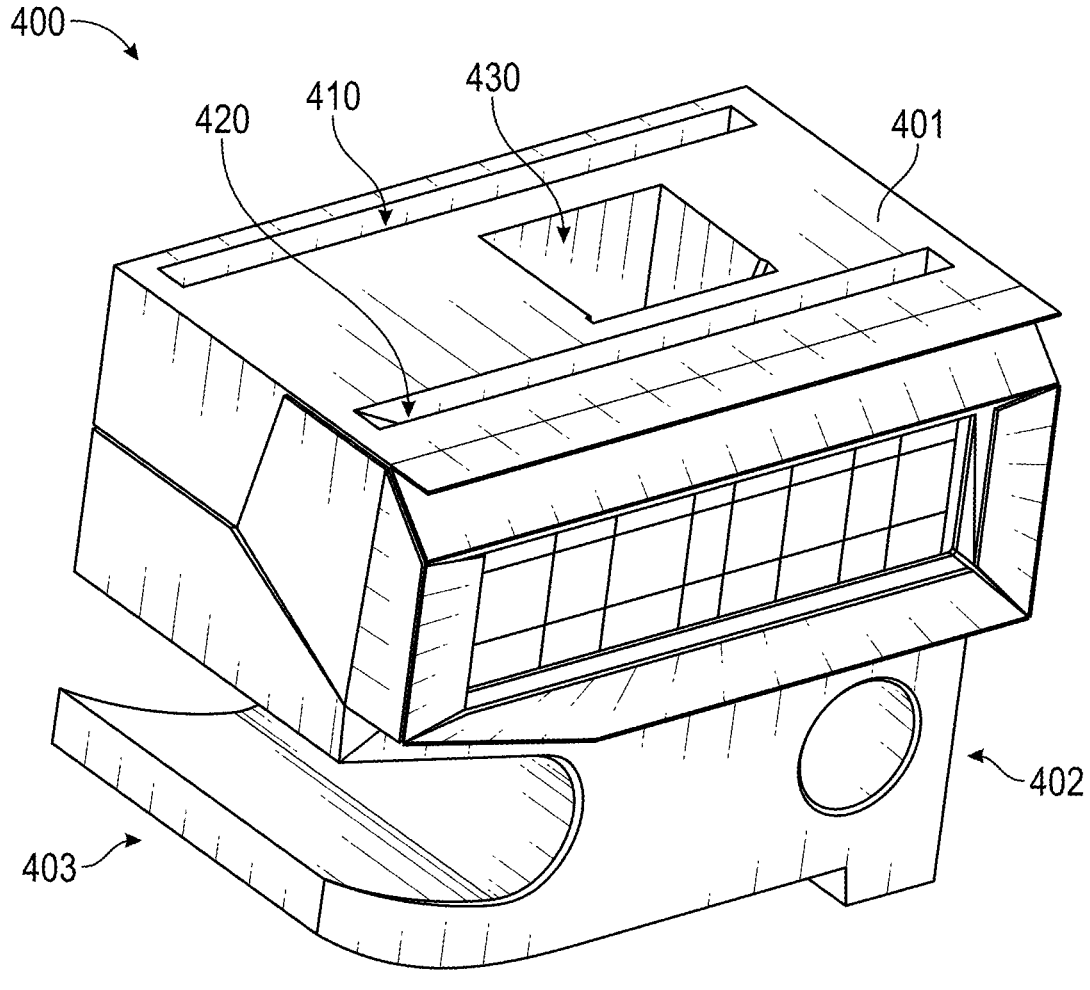
FIG. 4 is an illustration of a laryngoscope connector, according to one embodiment of the present disclosure.

FIG. 4 is an illustration of a connector 400 according to one embodiment of the present disclosure. The connector 400 can removably couple a blade, as described herein, to a laryngoscope handle. In one embodiment, the blade and connector can be disposable for hygiene purposes, while the handle is reusable. Therefore, the connector 400 can facilitate easy and secure coupling of the blade to the handle, as well as easy uncoupling of the blade from the handle. The connector 400 can also be configured to couple with known laryngoscopy handles. The blade can be coupled to a first surface 401 of the connector, while the handle is coupled to the base 402 of the connector. In one embodiment, the connector can be attached to the handle via one or more ball joints. The one or more ball joints can enable rotation of the connector and the blade relative to the rigid handle. In one embodiment, the base 402 of the connector can include a hook 403. The hook 403 can be inserted into a corresponding opening or slot in the handle of the laryngoscope. In one embodiment, the illumination source can be contained in the handle. Light can travel from the handle through the connector and to the first surface 401 via an internal channel in the body of the connector. In one embodiment, the illumination source can extend from the handle and can be inserted into or contained in the connector.

In one embodiment, the first surface 401 of the connector 400 can form a first slot (opening) 410 and a second slot (opening) 420 extending into the body of the connector. The projections 221, 222 of the base of the blade can be inserted into the first and second slot to attach the blade to the first surface of the connector. The first and second slot may or may not extend through the body of the connector. In one embodiment, the projections 221, 222 and the respective slots 410, 420 can form a snap-fit joint so that the projects are securely held in the slots. In one embodiment, the projects can be fused to the slots. In one embodiment, the connector 400 can form an internal channel from the base 402 terminating in an opening 430 at the first surface 401 of the connector 400. The internal channel and opening can provide a path for light to travel through the connector. In one embodiment, the opening 430 can be aligned with the cutout 250 at the base of the blade. In this manner, light emerging from the opening 430 can be directed through the base and body of the blade via the cutout 250.

In one embodiment, the laryngoscope blade of the present disclosure can meet rigidity, strength, and luminance requirements for laryngoscopic procedures. For example, the blade can be attached to a handle via the connector described herein. When the handle is fixed, a perpendicular tensile force of 65 N (Newtons) can be applied from the tip of the blade (e.g., a pulling force) without displacement of the blade exceeding 10 mm. In one embodiment, the tensile force can be 150 N without breakage or deformation of the blade. In one embodiment, a portion of the laryngoscope blade can be coated with aluminum such that a maximum illuminance of a region approximately 20 mm away from the blade is between 700 lux and 900 lux.

While this specification contains many specific implementation details, these should not be construed as limitations on the scope of what may be claimed, but rather as descriptions of features that may be specific to particular embodiments.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system modules and components in the embodiments described above should not be understood as requiring such separation in all embodiments, and it should be understood that the described program components and systems can generally be integrated together in a single component or packaged into multiple components.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Obviously, numerous modifications and variations are possible in light of the above teachings. It is therefore to be understood that within the scope of the appended claims, embodiments of the present disclosure may be practiced otherwise than as specifically described herein.

Embodiments of the present disclosure may also be as set forth in the following parentheticals:

(1) A laryngoscope, comprising: a blade having a flat top surface and a bottom surface extending from a base of the blade and a first vertical projection and a second vertical projection at the base of the blade extending from the bottom surface of the blade; and a connector configured to couple to a handle of the laryngoscope and further configured to couple to the base of the blade via a first opening, the first opening being configured to receive the first vertical projection and a second opening configured to receive the second vertical projection, wherein the base of the blade and a first portion of the blade are transparent or translucent and a second portion of the blade is opaque, and the base of the blade further includes a cutout aligned with a channel in the connector between the first opening and the second opening when the blade is coupled to the connector.

(2) The laryngoscope of (1), wherein the base of the blade and the first portion of the blade are acrylic.

(3) The laryngoscope of (1) to (2), wherein the second portion of the blade is coated in aluminum.

(4) The laryngoscope of (1) to (3), wherein the second portion of the blade is approximately two-thirds of a length of the blade.

(5) The laryngoscope of (1) to (4), wherein the second portion of the blade includes a tip of the blade.

(6) The laryngoscope of (1) to (5), wherein the bottom surface of the blade is reinforced with aluminum.

(7) The laryngoscope of (1) to (6), wherein the channel of the connector is optically coupled to an illumination source.

(8) The laryngoscope of (1) to (7), wherein the illumination source is a fiber optic cable.

(9) The laryngoscope of (1) to (8), wherein the blade is curved.

(10) A laryngoscope, comprising: a curved blade having a flat top surface and a bottom surface extending from a base of the curved blade and a first vertical projection and a second vertical projection at the base of the curved blade extending from the bottom surface of the curved blade; and a connector configured to couple to a handle of the laryngoscope and further configured to couple to the base of the curved blade via a first opening, the first opening being configured to receive the first vertical projection and a second opening configured to receive the second vertical projection, wherein the base of the curved blade and a first portion of the curved blade are transparent or translucent and a second portion of the curved blade is opaque.

(11) The laryngoscope of (10), wherein the base of the curved blade and the first portion of the curved blade are acrylic.

(12) The laryngoscope of (10) to (11), wherein the second portion of the curved blade is coated in aluminum.

(13) The laryngoscope of (10) to (12), wherein the second portion of the curved blade is approximately two-thirds of a length of the curved blade.

(14) The laryngoscope of (10) to (13), wherein the second portion of the curved blade includes a tip of the curved blade.

(15) The laryngoscope of (10) to (14), wherein the bottom surface of the curved blade is reinforced with aluminum.

(16) A laryngoscope, comprising: a blade having a flat top surface and a bottom surface extending from a base of the blade and a first vertical projection and a second vertical projection at the base of the blade extending from the bottom surface of the blade; and a connector configured to couple to a handle of the laryngoscope and further configured to couple to the base of the blade via a first opening, the first opening being configured to receive the first vertical projection and a second opening configured to receive the second vertical projection, wherein the base of the blade and a first portion of the blade are transparent or translucent and a second portion of the blade is opaque.

(17) The laryngoscope of (16), wherein the base of the blade and the first portion of the blade are acrylic.

(18) The laryngoscope of (16) to (17), wherein the second portion of the blade is coated in aluminum.

(19) The laryngoscope of (16) to (18), wherein the second portion of the blade is approximately two-thirds of a length of the blade.

(20) The laryngoscope of (16) to (19), wherein the second portion of the blade includes a tip of the blade.

Thus, the foregoing discussion discloses and describes merely exemplary embodiments of the present disclosure. As will be understood by those skilled in the art, the present disclosure may be embodied in other specific forms without departing from the spirit thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. A laryngoscope, comprising:
a blade having a flat top surface and a bottom surface extending from a base of the blade, the flat top surface and the bottom surface joined by a first sidewall and a second sidewall forming a hollow channel, and a first vertical projection and a second vertical projection at the base of the blade extending from the bottom surface of the blade; and
a connector configured to couple to a handle of the laryngoscope and further configured to couple to the base of the blade via a first opening, the first opening being configured to receive the first vertical projection and a second opening configured to receive the second vertical projection,
wherein the base of the blade and a first portion of the blade are transparent or translucent and a second portion of the blade is opaque, and
the base of the blade further includes a cutout aligned with a channel in the connector between the first opening and the second opening when the blade is coupled to the connector.

2. The laryngoscope of claim 1, wherein the base of blade and the first portion of the blade are acrylic.

3. The laryngoscope of claim 1, wherein the second portion of the blade is coated in aluminum.

4. The laryngoscope of claim 1, wherein the second portion of the blade is approximately two-thirds of a length of the blade.

5. The laryngoscope of claim 1, wherein the second portion of the blade includes a tip of the blade.

6. The laryngoscope of claim 1, wherein the bottom surface of the blade is reinforced with aluminum.

7. The laryngoscope of claim 1, wherein the channel of the connector is optically coupled to an illumination source.

8. The laryngoscope of claim 7, wherein the illumination source is a fiber optic cable.

9. The laryngoscope of claim 1, wherein the blade is curved.

10. The laryngoscope of claim 1, wherein the hollow channel is fully hollow.

11. A laryngoscope, comprising:
a curved blade having a flat top surface and a bottom surface extending from a base of the curved blade, the flat top surface and the bottom surface joined by a first sidewall and a second sidewall forming a hollow channel, and a first vertical projection and a second vertical projection at the base of the curved blade extending from the bottom surface of the curved blade; and
a connector configured to couple to a handle of the laryngoscope and further configured to couple to the base of the curved blade via a first opening, the first opening being configured to receive the first vertical projection and a second opening configured to receive the second vertical projection,
wherein the base of the curved blade and a first portion of the curved blade are transparent or translucent and a second portion of the curved blade is opaque.

12. The laryngoscope of claim 11, wherein the base of the curved blade and the first portion of the curved blade are acrylic.

13. The laryngoscope of claim 11, wherein the second portion of the curved blade is coated in aluminum or the bottom surface of the curved blade is reinforced with aluminum.

14. The laryngoscope of claim 11, wherein the second portion of the curved blade is approximately two-thirds of a length of the curved blade.

15. The laryngoscope of claim 11, wherein the second portion of the curved blade includes a tip of the curved blade.

16. A laryngoscope, comprising:
a blade having a flat top surface and a bottom surface extending from a base of the blade, the flat top surface and the bottom surface joined by a first sidewall and a second sidewall forming a hollow channel, and a first vertical projection and a second vertical projection at the base of the blade extending from the bottom surface of the blade; and
a connector configured to couple to a handle of the laryngoscope and further configured to couple to the base of the blade via a first opening, the first opening being configured to receive the first vertical projection and a second opening configured to receive the second vertical projection,
wherein the base of the blade and a first portion of the blade are transparent or translucent and a second portion of the blade is opaque.

17. The laryngoscope of claim 16, wherein the base of the blade and the first portion of the blade are acrylic.

18. The laryngoscope of claim 16, wherein the second portion of the blade is coated in aluminum.

19. The laryngoscope of claim 16, wherein the second portion of the blade is approximately two-thirds of a length of the blade.

20. The laryngoscope of claim 16, wherein the second portion of the blade includes a tip of the blade.

* * * * *